United States Patent
Tuma (10) Patent No.: US 6,303,080 B1
(45) Date of Patent: Oct. 16, 2001

(54) HYDROFLUOROETHERS AS HEAT-TRANSFER FLUIDS IN LOW TEMPERATURE PROCESSES REQUIRING STERILIZATION

(75) Inventor: Phillip E. Tuma, St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/633,436

(22) Filed: Aug. 7, 2000

Related U.S. Application Data (60) Provisional application No. 60/158,462, filed on Oct. 8, 1999.

(51) Int. Cl.[7] ............................................. A61L 2/00
(52) U.S. Cl. ........................ 422/38; 422/38; 422/407; 62/114; 62/185; 62/480
(58) Field of Search ............... 422/38, 407; 62/114, 62/185, 480

(56) References Cited

U.S. PATENT DOCUMENTS

| | | | | |
|---|---|---|---|---|
| 3,724,235 | * | 4/1973 | Carpigiani | 62/162 |
| 5,650,089 | * | 7/1997 | Gage et al. | 62/114 |
| 5,718,293 | * | 2/1998 | Flynn et al. | 252/2 |

FOREIGN PATENT DOCUMENTS

| | | |
|---|---|---|
| WO 97/14762 | 4/1997 | (WO) . |
| WO 99/48992 | 9/1999 | (WO) . |

OTHER PUBLICATIONS

*Journal of Fluorine Chemistry 95*, 1999, pp. 41–50.

\* cited by examiner

Primary Examiner—Robert J. Warden, Sr.
Assistant Examiner—Imad Soubra
(74) Attorney, Agent, or Firm—Lisa M. Fagan

(57) ABSTRACT

An apparatus for low temperature processing and high temperature sterilization comprising a hydrofluoroether heat-transfer fluid. Another embodiment of the present invention is a method therefor.

18 Claims, 2 Drawing Sheets

HYDROFLUOROETHERS AS HEAT-TRANSFER FLUIDS IN LOW TEMPERATURE PROCESSES REQUIRING STERILIZATION

CROSS REFERENCE TO RELATED PROVISIONAL APPLICATION

This application claims the benefit of U.S. Provisional Application No. 60/158,462, filed Oct. 8, 1999.

FIELD OF THE INVENTION

This invention relates to heat-transfer fluids. More particularly, this invention relates to hydrofluoroethers as heat-transfer fluids in low temperature processes requiring high temperature (e.g., steam) sterilization.

BACKGROUND

Low temperature processing can generally be described as a dehydration, a chemical reaction, a biological reaction, etc. which occurs in a vessel or chamber at temperatures ranging from about −80° C. to about 0° C. The low temperature processes of particular interest in the present invention occur in a vessel or chamber which requires sterilization (or a high temperature process) at the end of the low temperature processing. Examples of such chambers include, but are not limited to, a vacuum chamber for freeze drying and a chemical or biological reactor.

Freeze drying can generally be described as a process of dehydration or of separating water from a product containing biological matter or chemical matter. The product is frozen and then subjected to a high vacuum. The water vaporizes without melting (sublimes) leaving behind non-water components.

Generally, a freeze drying system requires at least four components: a vacuum chamber, a condenser, a vacuum pump, and a means for providing the heat of sublimation to the product being dried or a means for heat transfer. This heat transfer means may comprise a means for heating and a means for cooling. The vacuum chamber typically contains a series of thin stainless steel shelves. Product, for example in containers, is placed upon these shelves. The condenser is used to remove the sublimed water vapor. The pump is typically a high capacity vacuum pump. The freeze drying system typically comprises a sterilization process, especially for pharmaceutical applications.

Freeze drying systems operate over a range of temperatures, but in general the product is completely frozen prior to dehydration. The freezing point of the product may be well below the freezing point of water. For example, the freezing point of the product may be as low as about −50° C. or the operating temperature may be as low as about −50° C.

If sterilization is desired, the freeze drying system may also operate at temperatures around about 121° C. to about 130° C. at atmospheric pressure (i.e., the temperature for high-pressure saturated steam which is often used for sterilization).

During dehydration, a heat-transfer fluid is pumped through passages in the shelves of the vacuum chamber providing the heat of sublimation to the product being dried. Following drying, the product is removed from the container and the vacuum chamber may then be sterilized. As discussed, typically a high temperature steam (121° C. to 130° C. saturation temperature) is used for this sterilization process. If the heat-transfer fluid in the passages boils during this sterilization process, the system pressure may rise to a level where the shelves (which are typically thin to ensure adequate heat transfer) are damaged. Thus, selection of heat-transfer fluid is critical.

Heat-transfer fluids used in such applications typically are liquids having low viscosities at lower temperatures (i.e., −50° C. for the shelves and −80° C. for the condenser system), but are readily maintained in the liquid phase at the highest operating temperature for the system (which is typically during sterilization). Desirable heat-transfer fluids for freeze drying applications are also non-corrosive, non-toxic, and non-flammable.

Polydimethylsiloxanes (silicone oils) have a suitably wide liquid range and are often used in freeze drying. The average molecular weight of the silicone oil can be selected such that it functions well at temperatures as low as −80° C. At this temperature, the heat-transfer fluid may be pumped through passages in the shelves or condenser. Such a silicone oil has a boiling point significantly above 130° C. at atmospheric pressure, thus the passages may be kept full of heat-transfer fluid during the sterilization process without the danger of the heat-transfer fluid boiling and causing elevated system pressure and consequent shelf rupture. Silicone oils seem to be ideally suited for this type of application. However, they are flammable. There have been instances of fires caused by silicone oil and such fires can cost millions of dollars in damages as well as result in injury.

As is the case with freeze drying, during low temperature chemical or biological processes, the heat-transfer fluid preferably has good low temperature heat transfer characteristics. Typically, the heat-transfer fluid is pumped through a reactor jacket for heating, cooling, or temperature control. For ease of handling and safety, preferably this fluid is non-toxic and non-flammable. The heat-transfer fluid has similar temperature constraints (i.e., suitable at low temperature processing temperatures and at high temperature sterilization temperatures).

Fluorinated organic compounds, such as perfluorocarbons (PFCs), perfluoropolyethers (PFPEs), hydrofluorocarbons (HFCs), chlorofluorocarbons (CFCs), hydrochlorofluorocarbons (HCFCs), and hydrohalofluoroethers (HHFEs), or mixtures thereof, are generally non-toxic and non-flammable. The lower molecular weight compounds tend to have good low temperature heat transfer properties. Additionally, fluorinated organic compounds are non-corrosive and thermally stable.

However, some of these fluorinated organic compounds, such as HFCs, HCFCs, and HHFEs, tend not to be viable candidates as heat-transfer fluids because either their boiling points are too low (leading to excessive heat-transfer system pressure at high temperatures) or their freezing points are too high (leading to freeze-up or high viscosity at low temperatures). Candidates, for example, that are liquid at 130° C. or which have acceptable vapor pressures at this temperature tend to be solid or very viscous at −80° C. and thus cannot be used. Similarly, candidates, for example, that may work well at −80° C. tend to have lower boiling points which result in excessive vapor pressures that would prevent their use at 130° C. Typically, these fluids are not used in conventional designs because, to maintain the fluid in a liquid state throughout the system/apparatus and throughout the operating temperature range, the heat-transfer system is typically pressurized above the fluid saturation pressure using a compressed gas such as air or nitrogen. This pressure compromises the integrity of certain components in the apparatus unless they are built to more rigorous design codes which adds cost and may affect performance.

Other fluorinated organic compounds, such as PFCs and PFPEs, have long atmospheric lifetimes and/or high global warming potentials. CFCs may no longer be produced commercially due to ozone depletion concerns.

Thus, the need exists for a heat-transfer fluid for low temperature processes requiring high temperature sterilization which has good heat transfer properties at low temperatures, non-corrosivity, non-flammability, low toxicity, good environmental properties, and does not boil at sterilization temperatures.

SUMMARY OF THE INVENTION

The present invention provides an apparatus and a method for using certain hydrofluoroethers (HFEs) as heat-transfer fluids for low temperature processing where the chamber requires subsequent sterilization. The heat-transfer fluids of the present invention have good low temperature heat transfer properties, non-corrosivity, non-flammability, low toxicity, and good environmental (both low global warming potential and non-ozone depleting) properties. The HFEs of the present invention have a wide liquid range, having boiling points at atmospheric pressure greater than about 121° C.; or alternatively having a vapor pressure at 121° C. below two atmospheres, freezing points less than about –50° C.; and viscosities less than about 50 cSt throughout the operating temperature range. Thus, they are ideally suited as heat-transfer fluids in conventional low temperature processes requiring high temperature sterilization, such as freeze dryers.

The present invention provides an apparatus for low temperature processing and high temperature sterilization comprising: a product; a hydrofluoroether heat-transfer fluid which is liquid during low temperature processing and during sterilization; and a chamber requiring sterilization comprising one or more passageway(s) for said heat-transfer fluid; wherein during the chamber sterilization the heat-transfer fluid remains in said passageway(s).

Another embodiment of the present invention is a method of sterilizing a low temperature processing chamber comprising the steps of: (a) providing a chamber comprising one or more passageway(s); (b) providing a means for low temperature processing in said chamber; (c) providing a product requiring said low temperature processing; (d) providing a means for sterilizing said chamber; (e) providing a hydrofluoroether heat-transfer fluid in said passageway(s) which is liquid during low temperature processing and during sterilization; (f) processing said product using said low temperature processing means; (g) allowing said heat-transfer fluid to remain in said passageway(s); (h) sterilizing said chamber; (i) completing the sterilization of said chamber; and (j) allowing said chamber to cool.

BRIEF DESCRIPTION OF THE DRAWINGS

These figures are not to scale and are intended to be merely illustrative and non-limiting.

DETAILED DESCRIPTION OF ILLUSTRATIVE EMBODIMENTS

The present invention provides an apparatus and a method for low temperature processing using select HFEs as heat-transfer fluids. The apparatus of the present invention comprises a chamber, heat-transfer system or thermal fluid conditioner, and a pump.

The chamber of the present invention is sterilized after completion of the low temperature processing. Sterilization is defined herein as a process (e.g., high temperature steam) for killing microorganisms which may contaminate the chamber and for removing residual biological matter from the previous cycle in a biological application.

Optionally, the apparatus may further comprise stoppering or capping systems, an automated cleaning system (e.g., multiple high pressure spray nozzles, etc.), a process control system, a series of condensers, additional pumps, an expansion device, etc.

Product

The product of the present invention is generally a biological or a chemical material which is being processed at a low temperature, for example from about –80° C. to about 0° C. The product of the present invention is processed in a sterile environment. An example of such a material is a freeze dried pharmaceutical drug, food, biological material, parenteral (injectable) material, or delivery systems for such materials. The product may be placed directly into the chamber, or alternatively, the product may first be placed into a vial or container which is then placed in the chamber.

Heat-Transfer Fluid

As discussed above, the present invention utilizes a liquid hydrofluoroether heat-transfer fluid. The heat-transfer fluid is used to heat, cool, and/or maintain a temperature during processing. The heat-transfer fluid is inert, non-flammable, non-aqueous, and environmentally acceptable. Additionally, the heat-transfer fluid of the present invention has good heat transfer properties at low temperatures (e.g., about –80° C. to about 0° C.). To obtain adequate heat transfer performance and manageable pumping power requirements, the viscosity of the heat-transfer fluid is below about 50 cSt throughout the operating temperature range Preferably, the viscosity is below about 30 cSt throughout this range.

The heat-transfer fluid is preferably non-flammable, which is defined herein as having a flash point of greater than about 140° F. (about 60° C.).

The heat-transfer fluid has a boiling point greater than 121° C. at atmospheric pressure or, alternatively, has a vapor pressure at 121° C. below 2 atmospheres; has a freezing point less than about –50° C., preferably less than about –80° C.; and has a viscosity less than about 50 cSt throughout the operating temperature range.

The heat-transfer fluids of the present invention are hydrofluoroethers (HFEs). HFEs have a combination of good heat transfer performance over a wide liquid temperature range along with optimum safety (non-flammability and low toxicity) and environmental (non-ozone depleting and low global warming) properties. HFEs are chemical compounds, or mixtures of such compounds, containing carbon, fluorine, hydrogen, one or more ether oxygen atoms, and optionally one or more additional catenated (i.e., in-chain) heteroatoms within the carbon backbone, such as hexavalent sulfur or trivalent nitrogen. The HFEs can be straight-chained, branched-chained, or cyclic, or a combination thereof, such as alkylcycloaliphatic. Preferably, the HFEs are free of unsaturation. These highly fluorinated ethers may be depicted by Formula I:

$$(R_1\text{—O})_n\text{—}R_2 \qquad (I)$$

wherein n is a number from 1 to 3 inclusive and $R_1$ and $R_2$ are the same or are different from one another and are selected from the group consisting of alkyl, aryl, and aralkyl groups. At least one of $R_1$ and $R_2$ contains at least one fluorine atom, at least one of $R_1$ and $R_2$ contains at least one hydrogen atom, and preferably the total number of fluorine atoms in the HFE compound at least equals the total number of hydrogen atoms. $R_1$ and $R_2$ may be linear, branched, or cyclic, and may contain one or more catenated divalent oxygen or trivalent nitrogen atoms. The number of carbon atoms in the hydrofluoroether ranges from about 6 to about 12.

Preferred HFEs include: (1) segregated HFEs, wherein ether-bonded alkyl or alkylene, etc., segments of the HFE are either perfluorinated (e.g., perfluorocarbon) or non-fluorinated (e.g., hydrocarbon), but not partially fluorinated; and (2) non-segregated HFEs, wherein at least one of the ether-bonded segments is neither perfluorinated nor fluorine-free but is partially fluorinated (i.e., contains a mixture of fluorine and hydrogen atoms).

Segregated HFEs include HFEs which comprise at least one mono-, di-, or trialkoxy-substituted perfluoroalkane, perfluorocycloalkane, perfluorocycloalkyl-containing perfluoroalkane, or perfluorocycloalkylene-containing perfluoroalkane compound. Segregated HFEs are described, for example, in PCT Publication No. WO 96/22356, incorporated by reference herein, and can be represented below in Formula II:

$$R_f\text{---}(O\text{---}R_h)_x \qquad \qquad (II)$$

wherein:

x is from 1 to about 3, and $R_f$ is a perfluorinated hydrocarbon group having a valency x, which can be straight, branched, or cyclic, etc., and preferably contains from 4 to about 11 carbon atoms, and more preferably contains from 5 to about 10 carbon atoms;

each $R_h$ is independently a linear or branched alkyl group having from 1 to about 3 carbon atoms;

wherein either or both of the groups $R_f$ and $R_h$ can optionally contain one or more catenated oxygen and/or nitrogen heteroatoms; and wherein the sum of the number of carbon atoms in the $R_f$ group and $R_h$ group(s) is preferably between about 6 and about 12.

Preferably, x is 1. More preferably $R_f$ groups include $C_5F_{11}$— linear and branched isomers, $C_6F_{13}$— linear and branched isomers; $C_7F_{15}$— linear and branched isomers; perfluorocyclohexyl; perfluoroalkylcyclohexyl; perfluorocyclohexylalkyl; perfluoroalkylcyclohexylenealkyl; perfluoroalkoxycyclohexylenealkyl; perfluoromorpholinoalkyl; perfluoropiperidinylalkyl; perfluorotetrahydrofuranylalkyl; and preferable $R_h$ groups include methyl and ethyl.

Representative compounds described by Formula II useful in the present invention include, but are not limnited to, the following compounds and mixtures thereof:

n-$C_5F_{11}OC_2H_5$
n-$C6F_{13}OCH_3$
n-$C_6F_{13}OC_2H_5$
n-$C_7F_{15}OCH_3$
n-$C_7F_{15}OC_2H_5$
$C_2F_5CF(OC_2H_5)CF(CF_3)_2$
$C_3F_7CF(OC_2H_5)CF(CF_3)_2$
$C_3F_7CF(OCH_3)CF(CF_3)_2$
$C_5F_{11}CF(CF_3)CF_2OCH_3$
$C_6F_{13}CF(CF_3)CF_2OCH_3$
$CH_3OC_4F_8OCH_3$

Particularly preferred compounds of Formula II are those segregated HFEs which have boiling points greater than 121° C. at atmospheric pressure, thus obviating the need for pressurization during the sterilization process. These particularly preferred segregated HFEs include, but are not limited to, the following compounds:

n-$C_7F_{15}OC_2H_5$
$C_3F_7CF(OC_2H_5)CF(CF_3)_2$

Segregated nydrofluoroethers described by Formula IT can be prepared by alkylation of perfluorinated alkoxides prepared by the reaction of a corresponding perfluorinated acyl fluoride or perfluorinated ketone with an anhydrous alkali metal fluoride (e.g., potassium fluoride or cesium fluoride) or anhydrous silver fluoride in an anhydrous polar aprotic solvent. (See, e.g., the preparative methods described in French Patent Publication No. 2,287,432 and German Patent Publication No. 1,294,949, which are incorporated by reference herein). Alternatively, a fluorinated tertiary alcohol can be allowed to react with a base (e.g., potassium hydroxide or sodium hydroxide) to produce a perfluorinated tertiary alkoxide which can then be alkylated by reaction with alkylating agent, such as described in U.S. Pat. No. 5,750,797, which is herein incorporated by reference.

Suitable alkylating agents for use in the preparation of segregated hydrofluoroethers include dialkyl sulfates (e.g., dimethyl and diethyl sulfates), alkyl halides (e.g., methyl and ethyl iodides), alkyl p-toluenesulfonates (e.g., methyl p-toluenesulfonate), alkyl perfluoroalkanesulfonates (e.g., methyl perfluoromethanesulfonate), and the like. Suitable polar aprotic solvents include acyclic ethers such as diethyl ether, ethylene glycol dimethyl ether, and diethylene glycol dimethyl ether; carboxylic acid esters such as methyl formate, ethyl formate, methyl acetate, diethyl carbonate, propylene carbonate, and ethylene carbonate; alkyl nitrites such as acetonitrile; alkyl amides such as N,N-dimethylformarnmide, N,N-diethylformamide, and N-methylpyrrolidone; alkyl sulfoxides such as dimethyl sulfoxide; alkyl sulfones such as dimethylsulfone, tetramethylene sulfone, and other sulfolanes; oxazolidones such as N-methyl-2-oxazolidone; and mixtures thereof.

Suitable perfluorinated acyl fluorides can be prepared by electrochemical fluorination (ECF) of the corresponding hydrocarbon carboxylic acid (or a derivative thereof), using either anhydrous hydrogen fluoride (Simons ECF) or $KF_2 \cdot HF$ (Phillips ECF) as the electrolyte. Perfluorinated acyl fluorides and perfluorinated ketones can also be prepared by dissociation of perfluorinated carboxylic acid esters (which can be prepared from the corresponding hydrocarbon or partially-fluorinated carboxylic acid esters by direct fluorination with fluorine gas). Dissociation can be achieved by contacting the perfluorinated ester-with a source of fluoride ion under reacting conditions (see the method described in U.S. Pat. No. 3,900,372 (Childs), the description of which is incorporated herein by reference) or by combining the ester with at least one initiating reagent selected from the group consisting of gaseous, nonhydroxylic nucleophiles; liquid, non-hydroxylic nucleophiles; and mixtures of at least one non-hydroxylic nucleophile (gaseous, liquid, or solid) and at least one solvent which is inert to acylating agents.

Initiating reagents which can be employed in the dissociation are those gaseous or liquid, non-hydroxylic nucleophiles and mixtures of gaseous, liquid, or solid, non-hydroxylic nucleophile(s) and solvent (hereinafter termed "solvent mixtures") which are capable of nucleophilic reaction with perfluorinated esters. The presence of small amounts of hydroxylic nucleophiles can be tolerated. Suitable gaseous or liquid, nonhydroxylic nucleophiles include dialkylamines, trialkylamines, carboxamides, alkyl sulfoxides, amine oxides, oxazolidones, pyridines, and the like, and mixtures thereof. Suitable non-hydroxylic nucleophiles for use in solvent mixtures include such gaseous or liquid, non-hydroxylic nucleophiles, as well as solid, non-hydroxylic nucleophiles, e.g., fluoride, cyanide, cyanate, iodide, chloride, bromide, acetate, mercaptide, alkoxide, thiocyanate, azide, trimethylsilyl difluoride, bisulfite, and bifluoride anions, which can be used in the form of alkali metal, ammonium, alkyl-substituted ammonium (mono-, di-, tri-, or tetra-substituted), or quaternary phosphonium salts, and mixtures thereof. Such salts are in general commercially available but, if desired, can be prepared by known methods, e.g., those described by M. C. Sneed and R. C. Brasted in *Comprehensive Inorganic Chemistry*, Volume Six (The Alkali Metals), pages 61–64, D. Van Nostrand Company, Inc., New York (1957), and by H. Kobler et al. in Justus Liebigs Ann. Chem. 1978, 1937. 1,4-diazabicyclo [2.2.2]octane and the like are also suitable solid nucleophiles.

Useful non-segregated HFEs include omega- and alpha, omega-substituted hydrofluoroalkyl ethers such as those described in U.S. Pat. No. 5,658,962 (Moore et al.), incorporated herein by reference, and those described by Marchionni et al. in "Hydrofluoropolyethers," Journal of Fluorine Chemistry 95 (1999), pp. 41–50, which can be described by the general structure shown in Formula III:

$$X—[R_f'—O]_y R''H \quad (III)$$

wherein:
X is either F, H, or a perfluoroalkyl group containing from 1 to 4 carbon atoms which is optionally hydro-substituted in the omega position;

each $R_f'$ is independently selected from the group consisting of $—CF_2—$, $—C_2F_4—$, and $—C_3F_6—$, wherein, when X is a perfluoroalkyl group, X and at least a portion of the adjacent $R_f'$ group taken together can form a perfluorocycloalkyl group;

R" is a divalent organic radical having from 1 to about 4 carbon atoms and is preferably perfluorinated; and y is at least 1 and is chosen such that the total number of carbon atoms in Formula III is preferably between 6 and about 12, more preferably between 7 and 12;

wherein when X is F, R" contains at least one F atom.

Representative compounds described by Formula III useful in the present invention include, but are not limited to, the following compounds and mixtures thereof:

$C_7F_{15}OC_2F_4H$
$C_6F_{13}OC_2F_4OCF_2H$
$H(CF_2)_4O(CF_2)_4H$
$HCF_2OCF_2O(C_2F_4O)_2CF_2H$
$HCF_2OCF_2O(C_2F_4O)_3CF_2H$
$HCF_2O(CF_2O)_2(C_2F_4O)_2CF_2H$
$HCF_2O(CF_2CF_2O)_3CF_2H$
$HCF_2O(CF_2CF_2O)_4CF_2H$
$HCF_2O(CF_2CF_2O)_2CF_2H$
$HCF_2O(CF_2O)_2C_2F_4OCF_2H$

Some non-segregated HFE specialty liquids available from Ausimont Corp., Milan, Italy, under the trade name GALDEN H™, are suitable as heat-transfer fluids of the present invention.

Omega- and alpha, omega-substituted hydrofluoroalkyl ethers described by Formula III can be prepared by decarboxylation of the corresponding precursor fluoroalkyl ether carboxylic acids and salts thereof or, preferably, the saponifiable alkyl esters thereof, as described in U.S. Pat. No. 5,658,962, which is incorporated herein by reference.

Another process for making omega- and alpha, omega-substituted hydrofluoroalkyl ethers is described in U.S. Pat. No. 5,856,587 which is incorporated herein by reference. In this process, hydrofluoropolyethers are obtained by means of decarboxylation processes of alkaline salts obtained by hydrolysis and salification of the corresponding acylfluorides, by means of processes known in the art. For instance, decarboxylation is carried out in the presence of hydrogen-donor compounds, for instance water, at temperatures of 140°–170° C. and under pressure of at least 4 atm (3000 torr).

Alternatively, omega-hydrofluoroalkyl ethers can be prepared by reduction of a corresponding omega-chlorofluoroalkyl ether (e.g., those omega-chlorofluoroalkyl ethers described in WO 93/11868 published application), which is also described in U.S. Pat. No. 5,658,962.

Chamber

The chamber of the present invention is selected based on the system or application for which the apparatus or method of the present invention is being used. Generally, the chamber houses the product that is being processed at low temperature. The chamber of the present invention requires sterilization after the completion of the low temperature processing. The chamber may also comprise an automated cleaning system which is first used to clean the chamber prior to sterilization.

Typically, high temperature steam provides the means for sterilization. Generally, the high pressure steam with saturation temperatures ranging from about 121° C. to about 130° C. is used.

The apparatus of the present invention is particularly suitable for sterilization processes having high temperatures (e.g., those using about 121° C. to about 130° C. saturation temperature steam as described above).

The chamber of the present invention comprises one or more passageways. Passageways are defined herein as conduits for the heat-transfer fluid. The passageways may be within the chamber (e.g., shelves in a freeze dry vacuum chamber) or may be outside the chamber (e.g., a reactor jacket). The passageways allow the heat-transfer fluid to cool, heat, or maintain the temperature of the chamber as desired. Typically, the passageways cool down to about −50° C. in the case of freeze dryer shelves, but may reach about −80° C. for freeze dryer condensers or other applications such as reaction chambers.

The size, shape, and material of the chamber depend on the system or application and can be readily selected by one skilled in the art. For example, in freeze dry applications, the chamber is an insulated vacuum chamber whose walls are thick enough to withstand the pressure of the steam sterilization.

Pump

The present invention comprises a pump in fluid connection with the passageways via one or more pipes or lines. The size and type of the pump are determined by the system or application. For example, the pump may be a hermetic (e.g., canned or magnetically coupled) centrifugal pump.

Thermal Fluid Conditioner

The apparatus of the present invention may further comprise a thermal fluid conditioner. The thermal fluid conditioner comprises a means for heating and/or cooling the heat-transfer fluid. The means for heating and the means for cooling can be the same unit or can be one or more separate units.

The thermal fluid conditioner may comprise a heater and a direct expansion refrigeration system or a liquid nitrogen refrigeration system. This type of system is commonly known to those skilled in the art and is used to maintain the heat-transfer fluid at a prescribed temperature.

The thermal fluid conditioner is in fluid connection with the passageways.

Apparatus

The apparatus of the present invention is particularly useful for pharmaceutical freeze drying. The heat-transfer fluid is used to cool and heat the shelves in the freeze dryer (and optionally may be used to cool a condenser attached to the end of the shelves or directly attached to the vacuum chamber).

During low temperature operation or during freeze drying (FIG. 1, for example), the drying process begins by cooling the shelves in the freeze dryer to the desired temperature using the heat-transfer fluid and the primary thermal fluid conditioning system 18 (e.g., direct expansion refrigeration cycle). The product which is placed upon the shelves 13 in vials is frozen during this process. At the same time, the condenser coil is cooled to the desired temperature to ensure an adequate potential for removing the sublimed moisture from the product.

Figure 1:
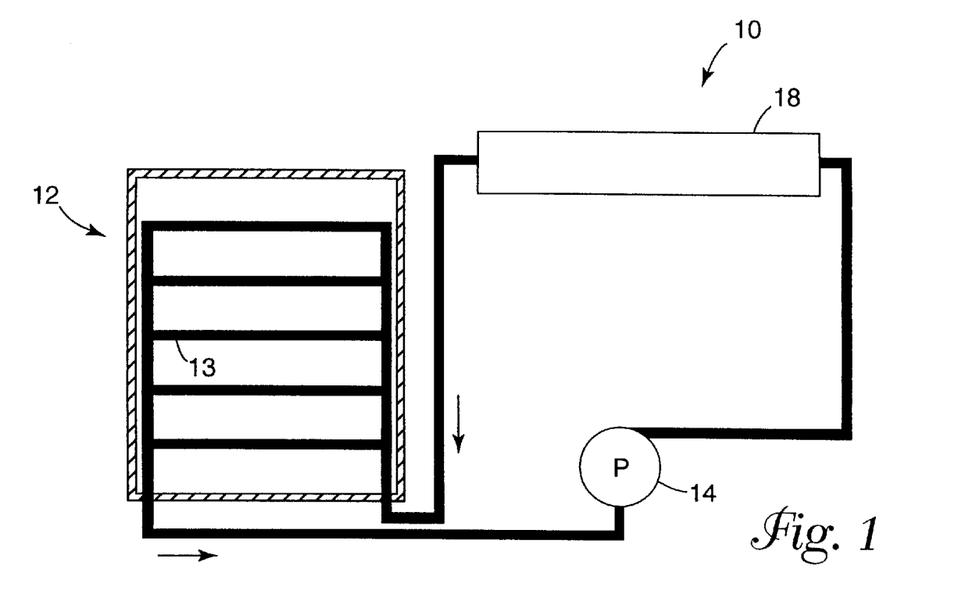
FIG. 1 is a schematic of an apparatus 10 of the present invention comprising a chamber 12 having passageways 13, a thermal fluid conditioner 18, and a pump 14.

Vacuum is then applied to begin the drying process. During this process, the temperature of the shelves 13 is varied as desired. After drying is completed, the shelf temperature is close to room temperature, the pump 14 is turned off, the vials are stoppered, and the product is removed from the chamber 12. The chamber 12 is now re-sealed and high pressure steam enters the freeze drying chamber. The heat-transfer fluid within the shelves remains in the shelves during sterilization. The heat-transfer fluid in the shelves has a boiling point above the sterilization temperature, thus the heat-transfer fluid does not boil and thus increase the system pressure. After sterilization is complete, the chamber is allowed to cool. The heat-transfer fluid vapor in the shelves also cools. The cycle may then begin again.

Figure 2:
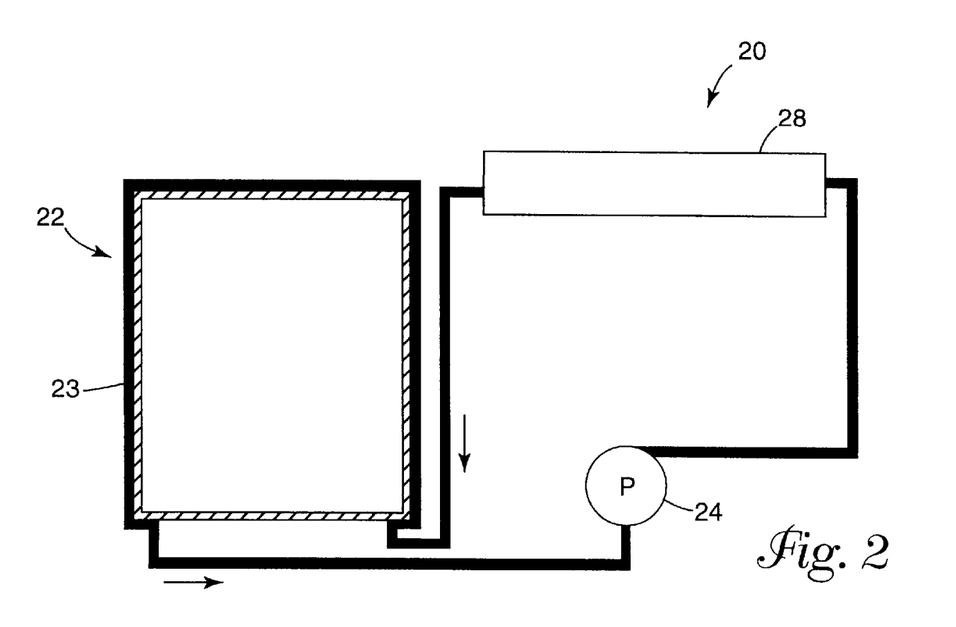
FIG. 2 is a schematic of an apparatus 20 of the present invention comprising a chamber 22 having passageways 23, a thermal fluid conditioner 28, and a pump 24.

The apparatus of the present invention is also particularly useful in low temperature reactions. This apparatus comprises a reactor vessel and a reactor jacket which comprises heat-transfer fluid. FIG. 2 illustrates one such apparatus. During low temperature operation, the heat-transfer fluid remains in the reactor jacket 23 to perform the desired temperature-related operation.

When the reaction is completed, the product is removed from the reactor chamber 22. The reactor chamber may be cleaned first and then the reactor chamber is sealed and steam enters the chamber for sterilization. The heat-transfer fluid within the reaction vessel jacket passageways remains in the passageways during sterilization.

After sterilization is complete, the reactor chamber is allowed to cool. The heat-transfer fluid also cools. The cycle may then begin again.

METHOD

The present invention comprises a method of sterilizing a low temperature processing chamber. This method comprises the steps of: (a) providing a chamber comprising one or more passageway(s); (b) providing a means for low temperature processing in said chambers; (c) providing a product requiring said low temperature processing; (d) providing a means for sterilizing said chamber; (e) providing a hydrofluoroether heat-transfer fluid in said passageway(s) which is liquid during low temperature processing and during sterilization; (f) processing said product using said low temperature processing means; (g) allowing said heat-transfer fluid to remain in said passageway(s); (h) sterilizing said chamber; (i) completing the sterilization of said chamber; and (j) allowing said chamber to cool.

EXAMPLES

The present invention will be further described with reference to the following nonlimiting examples and test methods. All parts, percentages, and ratios are by weight unless otherwise specified.

Example 1

Example 1 Compares a Heat-transfer Fluid of the Present Invention to Silicone Oils The top of Table 1 shows heat transfer properties for $C_3F_7CF(OC_2H_5)CF(CF_3)_2$, Galden™ HT-135, a popular perfluoropolyether fluid manufactured by Ausimont Chemicals, Milan, Italy (comparative), and several commercially available silicone oil fluids (comparative), available from Dow Chemical Company, Midland, Mich. and Miles Inc., Pittsburgh, Pa., commonly used in the freeze dryer industry. The physical properties were obtained from literature, except for $C_3F_7CF(OC_2H_5)CF(CF_3)_2$.

Preparation of $C_3F_7CF(OC_2H_5)CF(CF_3)_2$

Into a dry 600 milliliter Parr reactor were added 36.3 g (0.625 mol) of anhydrous potassium fluoride and 108 g of anhydrous diglyme (diethylene glycol dimethyl ether). The potassium fluoride was made by spray drying, was stored at 125° C., and was ground shortly before use. The contents in the reactor were cooled with dry ice, then 125 g (0.52 mol) of n-$C_3F_7COF$ (approximately 90 percent purity) were added. When the reactor reached a temperature of 52° C. and pressure of 65 psig (4190 torr), 101.5 g (0.68 mol) of $CF_3CF=CF_2$ (hexafluoropropylene) were added at 70° C. and at a pressure range of 18–75 psig (1690–4640 torr) over approximately a three hour period, followed by a two hour hold period at 70° C. The reactor and its contents were allowed to cool to room temperature, the reactor was opened, and to the reactor were added an additional 1.5 g of potassium fluoride, along with 14.5 g (0.016 mol) of ADOGEN™ 464 and 119.2 g (0.77 mol) of diethyl sulfate. ADOGEN™ 464, available from Witco. Corp., Oleo/Surfactant Group, Greenwich, Conn., is a tri(octyl-decyl) monomethyl quaternary ammonium chloride, 90 percent active; for this experiment, the ADOGEN™ 464 was diluted with anhydrous glyme and was vacuum fractionated of alcohol solvent to a 50 weight percent concentration. The Parr reactor was again sealed and was heated to 52° C. with maximum agitation for three days. The reactor was then pressure-charged with 60 g of 45 weight percent aqueous potassium hydroxide and 50 g of deionized water, was again sealed, and was heated to 85° C. for 1½hours. The reaction was allowed to cool overnight, the reactor was vented, and its contents were transferred to a flask for distillation. 235.2 g of product were recovered, representing a 96.9 percent yield based on the $C_3F_7COF$ charge. Percent purity was 88.7 percent, based on analysis by gas chromatograph.

The recovered crude product was fractionated on a 10-plate vacuum jacketed Oldershaw column, water-washed, and dried over anhydrous magnesium sulfate. A portion of the distilled and washed product was accurately weighed when placed into an NMR tube and was spiked with a known amount of 1,4-bis(trifluoromethyl)benzene (p-HFX) for use as a cross integration or internal standard. Then a 400 MHz$^1$-NMR spectrum (#h56881.401) and a 376 MHz$^{19}$F-NMR spectra spectrum (#f56881.402) were measured at room temperature using a Varian UNITYplus 400 FT-NMR spectrometer. This method of preparation permitted the p-HFX to be used as either 1) an internal standard for measuring the absolute weight percent concentrations of specific components or 2) as a cross integration standard to facilitate the cross correlation of the various fluorine and proton signal intensities for evaluation of the overall sample composition.

The results from the proton and fluorine NMR cross integration determination are shown below:

| Component Structures | $^1H/^{19}F$-NMR Relative Wt. % Concentrations (single trial measurement) |
|---|---|
| $CF_3CF_2CF_2CF(OCH_2CH_3)$—$CF(CF_3)_2$ | 99.86% |
| $[(CF_3)_2$—$CF$—$]_2$—$CF$—$O$—$CH_2CH_3$ | 0.093% |
| $CF_3CF_2CF_2CF(OCH_3)$—$CF(CF_3)_2$ | 0.044% |
| $CF_3OCF_2CF_2CF(OCH_2CH_3)CF(CF_3)_2$ | 0.0057% |
| Possible Acetone | 0.0005% |

Results from the NMR analysis indicate the washed distillate to contain 99.96 percent of $C_3F_7CF(OC_2H_5)CF(CF_3)_2$, the desired product.

Analysis of several other $C_3F_7CF(OC_2H_5)CF(CF_3)_2$ preparations made using essentially the same synthetic and purification procedures showed percent purities of 99.71, 99.89 and 99.96 percent The liquid density of $C_3F_7CF(OC_2H_5)CF(CF_3)_2$ was measured from 10° C. to 90° C. using an Anton-Parr Model DMA58 densitometer with a DMA602 external cell. Densities below this temperature were obtained by linear extrapolation of the available data.

The specific heat of $C_3F_7CF(OC_2H_5)CF(CF_3)_2$ was measured by differential scanning calorimetry according to ASTM E 1269-90 over a temperature range of −50° C. to 50° C.

The kinematic viscosity of $C_3F_7CF(OC_2H_5)CF(CF_3)_2$ was measured using a Cannon-Fenske viscometer over the temperature range −80° C. to 23° C. Data were regressed using methods outlined in ASTM Standard 341-77.

The thermal conductivity of $C_3F_7CF(OC_2H_5)CF(CF_3)_2$ was not measured. Instead, experimentally-determined values for the hydrofluoroether $C_4F_9OC_2H_5$ were used. These values were determined using a transient, hot-wire thermal conductivity cell over the temperature range of −50° C. to +50° C., according to ASTM D 2717-86. A platinum wire was used in the measurements. The wire was 20 centimeter length, 0.17 millimeter diameter, and had a resistance of 120 Ω at 20° C. The thermal conductivities are set forth in Tables 1–4.

All properties are calculated at −40° C. from available data. The HT-135 fluid is not used in freeze dryers, however, experimental data comparing it to the $C_3F_7CF(OC_2H_5)CF(CF_3)_2$ are available (to be discussed later). HT-135 is therefore included in the theoretical analysis.

The theoretical analysis (the lower portion of Table 1) shows fully-developed, adiabatic, steady pipe flow calculations comparing the aforementioned fluids flowing through a 0.445 centimeter diameter, smooth pipe. The HT-135 flow rate is selected such that it would produce a thermal capacity, C, of 70 W/° C. The thermal capacity is defined as:

$$C = \dot{m}c \qquad (1)$$

Here $\dot{m}$ is the mass flow rate and c is the specific heat of the fluid. The flow rates of $C_3F_7CF(OC_2H_5)CF(CF_3)_2$ and the silicone oils are adjusted such that their thermal capacities match that of the HT- 135.

The heat transfer coefficient, h, is calculated from the definition of the Nusselt number, Nu, $$Nu \equiv \frac{hd}{k} \qquad (2)$$

where d is the pipe diameter and k is the thermal conductivity of the fluid. The Nusselt number in the laminar regime (Re<2300) is constant at 4.36. In the transition and turbulent regimes (Re>2300), a correlation by Gnielinski is used (Gnielinski, V., Int. Chem. Eng., 1976, Volume 16, p.359).

$$Nu \equiv \frac{f/8(Re - 1000)Pr}{1 + 12.7(f/8)^{1/2}(Pr^{2/3} - 1)} \qquad (3)$$

This correlation is valid for 2300<Re<5×10$^6$ and 0.5<Pr<2000 and these conditions are met for the fluids shown. The Reynolds number, Re, is defined as:

$$Re \equiv \frac{\rho V d}{\mu} = \frac{V d}{v} \quad (4)$$

and the Prandtl number, Pr, as:

$$Pr \equiv \frac{\mu c}{k} = \frac{v \rho c}{k} \quad (5)$$

where $\mu$ is the dynamic viscosity, $v$ is the kinematic viscosity and $\rho$ is the fluid density. The gradient of pressure along the pipe length, dp/dx, is calculated using relations for the smooth pipe friction factor, f $$f = 0.184 \, Re^{-1/5} \quad Re > 2 \times 10^4 \quad (6)$$

$$f = 0.316 \, Re^{-1/4} \quad 2300 \leq Re \leq 2 \times 10^4 \quad (7)$$

$$f = \frac{64}{Re} \quad Re < 2300 \quad (8)$$

and the definition of the friction factor $$\frac{dp}{dx} = f \frac{\rho V^2}{2d} \quad (9)$$

where V is the average fluid velocity $$V = \frac{\dot{m}}{\rho} \frac{4}{\pi d^2} \quad (10)$$

The pumping power, P, per unit length, L, of pipe can then be calculated using $$P/L = \frac{dp}{dx} \frac{\dot{m}}{\rho} \quad (11)$$

Table 1—Theoretical Comparison of the Heat Transfer Performance of $C_3F_7CF(OC_2H_5)CF(CF_3)_2$ compared to Galden® HT-135 (comparative) and 3 silicone oil fluids (comparative) commonly used in commercial freeze dryers. Temperature is −40° C.

| | $C_3F_7CF(OC_2H_5)$ $CF(CF_3)_2$ | HT-135 (comparative) | Syltherm XLT (comparative) | Mobay M3 (comparative) | Mobay M5 (comparative) |
|---|---|---|---|---|---|
| PROPERTIES* | | | | | |
| Cp [J/kg-K] | 1.03E + 03 | 7.81E + 02 | 1.49E + 03 | 1.30E + 03 | 1.60E + 03 |
| Z (a parameter) | 4.25E + 00 | 6.70E + 00 | 6.18E + 00 | — | — |
| v [cSt] | 3.55E + 00 | 6.00E + 00 | 5.48E + 00 | 1.30E + 01 | 2.31E + 01 |
| v [m²/s] | 3.55E − 06 | 6.00E − 06 | 5.48E − 06 | 1.30E − 05 | 2.31E − 05 |
| ρ [kg/m³] | 1749 | 1940 | 896 | 969 | 989 |
| k [W/m-K] | 0.076 | 0.070 | 0.123 | 0.140 | 0.140 |
| THEORETICAL ANALYSIS | | | | | |
| d [m] | 4.45E − 03 | 4.45E − 03 | 4.45E − 03 | 4.45E − 03 | 4.45E − 03 |
| mdot [kg/s] | 6.79E − 02 | 8.96E − 02 | 4.68E − 02 | 5.40E − 02 | 4.38E − 02 |
| Cp*mdot [W/° C.] | 7.00E + 01 | 7.00E + 01 | 7.00E + 01 | 7.00E + 01 | 7.00E + 01 |
| V [m/s] | 2.50E + 00 | 3.29E + 00 | 3.36E + 00 | 3.58E + 00 | 2.85E + 00 |
| Re | 3.13E + 03 | 2.44E + 03 | 2.73E + 03 | 1.23E + 03 | 5.50E + 02 |
| Pr | 8.39E + 01 | 1.30E + 02 | 5.97E + 01 | 1.17E + 02 | 2.60E + 02 |
| f | 4.22E − 02 | 4.50E − 02 | 4.37E − 02 | 5.22E − 02 | 1.16E − 01 |
| Nu | 5.32E + 01 | 4.30E + 01 | 3.92E + 01 | 4.36E + 00 | 4.36E + 00 |
| h [W/m²-K] | 9.11E + 02 | 7.37E + 02 | 1.08E + 03 | 1.37E + 02 | 1.37E + 02 |
| dP/dx [Pa/m] | 5.17E + 04 | 9.58E + 04 | 4.97E + 04 | 7.29E + 04 | 1.05E + 05 |
| Power [W/m] | 2.01E + 00 | 4.91E + 00 | 2.60E + 00 | 4.06E + 00 | 4.65E + 00 |

*Galden ™ HT-135 data taken from Ausimont product literature.
Syltherm ™ XLT data taken from Dow product literature.
Mobay silicone oil properties taken from 9/5/97 data sheet provided by Hull Corp.

These theoretical data show that for a given thermal capacity, the heat transfer performance of $C_3F_7CF(OC_2H_5)CF(CF_3)_2$, as evidenced by the heat transfer coefficient, h, is comparable to that of the silicone oils. That the $C_3F_7CF(OC_2H_5)CF(CF_3)_2$ can accomplish this with a much lower pumping power requirement indicates that superior heat transfer performance can be obtained if the thermal capacity of $C_3F_7CF(OC_2H_5)CF(CF_3)_2$ is increased by increasing the flow rate.

Figure 3:
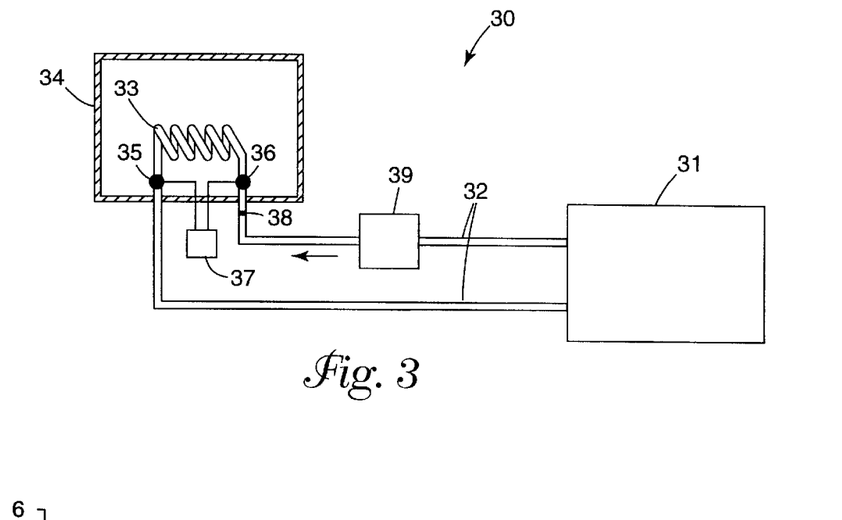
FIG. 3 is a schematic of an apparatus 30 of the present invention comprising an adiabatic enclosure 34 comprising coils 33, and chiller 31.

FIG. 3 shows the experimental apparatus used to compare the pumping power performance of $C_3F_7CF(OC_2H_5)CF(CF_3)_2$ and Galden™ HT-135. The apparatus consists of an FTS Model RC-210B-20W chiller 31, available from FTS Kinetics, Stoneridge, N.Y., connected with insulated polyethylene tubing 32 to a 1.4 meter length of 0.445 centimeter inner diameter copper coil 33. 0.014 inch (0.0356 centimeter) diameter holes drilled at positions 35 and 36 (1.3 meters apart on the coil) are connected to the ports of an Omega model XPC100DTH differential pressure transducer 37, available from Omega Engineering, Inc., Stamford, Conn. A type-J thermocouple 38 is installed in the inlet line just upstream of the coil. A micro motion model S025S119 mass flow meter 39, available from Micro Motion, Boulder, Colo., is installed in the inlet line to the coil.

Figure 4:
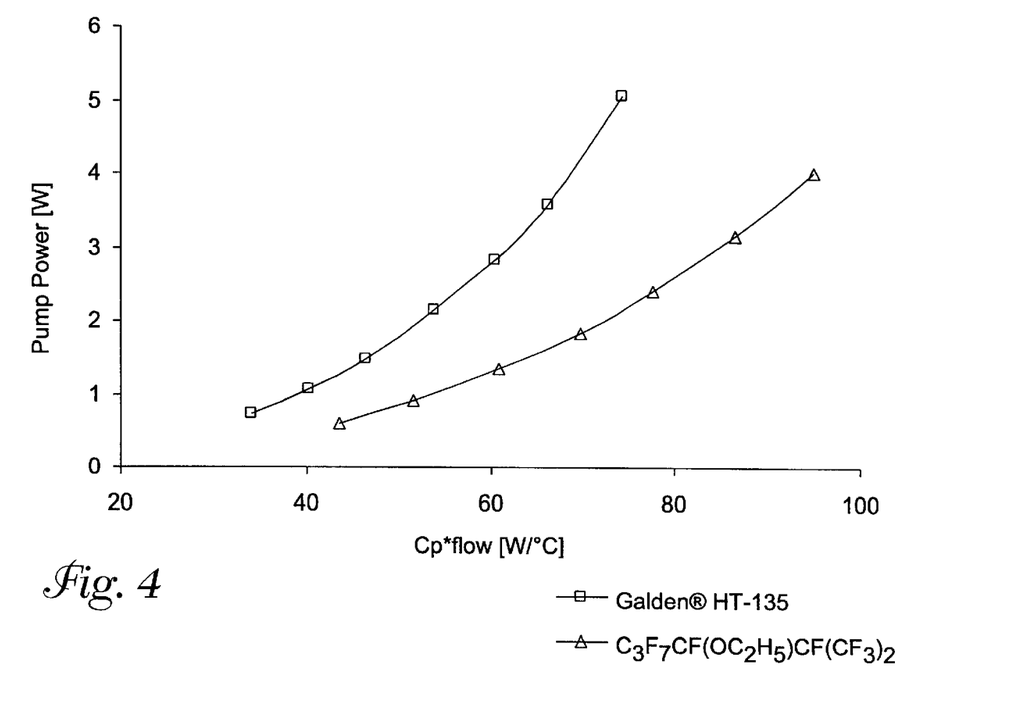
FIG. 4 is a graph illustrating the thermal capacity versus pumping power for heat-transfer fluids.

Data obtained from this apparatus are combined with specific heat and density data shown in Table 1 using equations 1 and 11. The results are shown in FIG. 4. These data are intended to confirm the utility of the theoretical method employed in Table 1 to compare the $C_3F_7CF(OC_2H_5)CF(CF_3)_2$ to the silicone oils. At a thermal capacity of 70 W/° C., the theoretical data show pumping power requirements of 4.9 and 2.0 W/m for the $C_3F_7CF(OC_2H_5)CF(CF_3)_2$ and HT-135 fluids, respectively. This is in good agreement with the experimental values of 4.3 and 1.9 W/m shown in FIG. 4.

Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. An apparatus for low temperature processing and high temperature sterilization comprising:
   (a) a product in a chamber;
   (b) a hydrofluoroether heat-transfer fluid that remains a liquid during low temperature processing and during sterilization;
   (c) a chamber requiring sterilization comprising one or more passageway(s) for said heat-transfer fluid; and
   (d) a pump in fluid connection with said passageway(s); wherein during the chamber sterilization the heat-transfer fluid remains in said passageway(s).

2. The apparatus according to claim 1, wherein said product is selected from the group consisting of a pharmaceutical drug, food, biological material, parenteral material, and a delivery system for materials.

3. The apparatus according to claim 1, wherein said low temperature processing is selected from the group consisting of freeze drying, chemical processing, and biological processing.

4. The apparatus according to claim 3, wherein said apparatus further comprises a thermal fluid conditioner.

5. The apparatus according to claim 4, wherein said thermal fluid conditioner comprises a means for cooling said heat-transfer fluid and wherein said means is in fluid connection with said passageway(s).

6. The apparatus according to claim 4, wherein said means of heating and means of cooling are one system.

7. The apparatus according to claim 4, wherein said thermal fluid conditioner comprises a means for heating said heat-transfer fluid and wherein said means is in fluid connection with said passageway(s).

8. The apparatus according to claim 1, wherein said low temperature processing is freeze drying and said passageway(s) are in shelves contained within the chamber.

9. The apparatus according to claim 1, wherein said low temperature processing is a chemical or a biological process and wherein said passageway is a reactor jacket.

10. The apparatus according to claim 1, wherein said high temperature sterilization is high temperature steam.

11. The apparatus according to claim 1, wherein said heat-transfer fluid has an atmospheric boiling point of greater than about 121° C.

12. The apparatus according to claim 1, wherein said heat-transfer fluid at about 121° C. has a vapor pressure less than about two atmospheres.

13. The apparatus according to claim 1, wherein said hydrofluoroether heat-transfer fluid comprises compounds of the formula:

wherein:
   n is a number from 1 to 3 inclusive;
   $R_1$ and $R_2$ are the same or are different from one another and are selected from the group consisting of alkyl, aryl, and alkylaryl groups;
   at least one of $R_1$ and $R_2$ contains at least one fluorine atom;
   at least one of $R_1$ and $R_2$ contains at least one hydrogen atom;
   $R_1$ and $R_2$ may contain one or more catenated divalent oxygen or trivalent nitrogen atoms; and
   the total number of carbons ranges from about 6 to about 12.

14. The apparatus according to claim 13, wherein said hydrofluoroether heat-transfer fluid is segregated and has the following formula:

wherein:
   x is from 1 to about 3, and $R_f$ is a perfluorinated hydrocarbon group having a valency x, which can be straight, branched, or cyclic;
   each $R_h$ is independently a linear or branched alkyl group having from 1 to about 3 carbon atoms;
   wherein either or both of the groups $R_f$ and $R_h$ can optionally contain one or more catenated heteroatoms; and
   wherein the sum of the number of carbon atoms in the $R_f$ group and the number of carbon atoms in the $R_h$ group(s) is between 6 and about 12.

15. The apparatus according to claim 14, wherein said hydrofluoroether heat-transfer fluid comprises an $R_f$ group selected from the group consisting of $C_5F_{11}$— linear and branched isomers, $C_6F_{13}$— linear and branched isomers; $C_7F_{15}$— linear and branched isomers; perfluorocyclohexyl; perfluoroalkylcyclohexyl; perfluorocyclohexylalkyl; perfluoroalkylcyclohexylenealkyl; perfluoroalkoxycyclohexylenealkyl; perfluoromorpholinoalkyl; perfluoropiperidinylalkyl; and perfluorotetrahydrofuranylalkyl.

16. The apparatus according to claim 14, wherein said hydrofluoroether heat-transfer fluid is selected from the group consisting of n-$C_7F_{15}OC_2H_5$, $C_3F_7CF(OC_2H_5)CF(CF_3)_2$, $C_5F_{11}CF(CF_3)CF_2OCH_3$, $C_6F_{13}CF(CF_3)CF_2OCH_3$, and 17. The apparatus according to claim 13, wherein said hydrofluoroether heat-transfer fluid is non-segregated and has the following formula:

wherein:
   X is either F, H, or a perfluoroalkyl group containing from 1 to 4 carbon atoms;

each $R_f'$ is independently selected from the group consisting of —$CF_2$—, —$C_2F_4$—, and —$C_3F_6$—, optionally wherein when X is a perfluoroalkyl group, X and at least a portion of the adjacent $R_f'$ group taken together can form a perfluorocycloalkyl group;

R" is a divalent organic radical having from 1 to about 4 carbon atoms; and y is at least 1;

wherein when X is F, R" contains at least one F atom; and wherein the sum of the number of carbon atoms in the $R_f'$ group(s) and the number of carbon atoms in the R" group is between 7 and about 12.

18. A method of sterilizing a low temperature processing chamber comprising the steps of:

(a) providing a chamber comprising one or more passageway(s);

(b) providing a means for low temperature processing in said chambers;

(c) providing a product in said chamber requiring said low temperature processing;

(d) providing a means for sterilizing said chamber;

(e) providing a hydrofluoroether heat-transfer fluid in said passageway(s) that remains a liquid during low temperature processing and during sterilization;

(f) processing said product using said low temperature processing means;

(g) allowing said heat-transfer fluid to remain in said passageway(s);

(h) sterilizing said chamber;

(i) completing the sterilization of said chamber; and (j) allowing said chamber to cool.

* * * * *

UNITED STATES PATENT AND TRADEMARK OFFICE
CERTIFICATE OF CORRECTION

PATENT NO. : 6,303,080 B1
DATED : October 16, 2001
INVENTOR(S) : Tuma, Phillip E.

It is certified that error appears in the above-identified patent and that said Letters Patent is hereby corrected as shown below:

Column 4,
Line 41, delete "range" and insert in place thereof -- range. --.

Column 5,
Line 58, delete "n-C6F$_{13}$OCH$_3$" and insert in place thereof -- n-C$_6$F$_{13}$OCH$_3$ --.

Column 6,
Line 48, delete "nydrofluoroethers" and insert in place thereof -- hydrofluoroethers --;
Line 48, delete "IT" and insert in place thereof -- II --.

Column 7,
Lines 7-8, delete "N,N-dimethylformarnmide" and insert in place thereof
-- N,N-dimethylformamide --.

Column 10,
Line 60, delete "Galden ™" and insert in place thereof -- Galden ® --.

Column 11,
Line 41, delete "MHz$^1$-NMR" and insert in place thereof -- MHz$^{1H}$-NMR --.

Column 12,
Line 4, delete "percent" and insert in place thereof -- percent. --.

UNITED STATES PATENT AND TRADEMARK OFFICE
CERTIFICATE OF CORRECTION

PATENT NO. : 6,303,080 B1
DATED : October 16, 2001
INVENTOR(S) : Tuma, Phillip E.

It is certified that error appears in the above-identified patent and that said Letters Patent is hereby corrected as shown below:

Column 16,
Line 16, delete
"

", and insert in place thereof

--

, --.

Signed and Sealed this

Eleventh Day of June, 2002

Attest:

JAMES E. ROGAN
Attesting Officer
Director of the United States Patent and Trademark Office